(12) United States Patent
Riddle et al.

(10) Patent No.: US 9,427,785 B2
(45) Date of Patent: Aug. 30, 2016

(54) REMEDIATION USING TRACE ELEMENT HUMATE SURFACTANT

(71) Applicants: Catherine Lynn Riddle, Idaho Falls, ID (US); Steven Cheney Taylor, Ammon, ID (US); Debra Fox Bruhn, Idaho Falls, ID (US)

(72) Inventors: Catherine Lynn Riddle, Idaho Falls, ID (US); Steven Cheney Taylor, Ammon, ID (US); Debra Fox Bruhn, Idaho Falls, ID (US)

(73) Assignee: U.S. Department of Energy, Washington, DC (US)

( * ) Notice: Subject to any disclaimer, the term of this patent is extended or adjusted under 35 U.S.C. 154(b) by 0 days.

(21) Appl. No.: 14/314,667

(22) Filed: Jun. 25, 2014

(65) Prior Publication Data

US 2015/0375281 A1 Dec. 31, 2015

(51) Int. Cl.
*B09C 1/00* (2006.01)
*B09C 1/08* (2006.01)
*G01N 33/24* (2006.01)

(52) U.S. Cl.
CPC ............... *B09C 1/08* (2013.01); *G01N 33/24* (2013.01)

(58) Field of Classification Search
CPC .................................. B09C 1/10; B09C 1/105
See application file for complete search history.

(56) References Cited

U.S. PATENT DOCUMENTS

| 5,368,411 | A  | * | 11/1994 | Losack   | B09C 1/02 134/40     |
|-----------|----|---|---------|----------|----------------------|
| 5,545,801 | A  | * | 8/1996  | Fulton   | B09C 1/10 175/206    |
| 6,758,633 | B2 | * | 7/2004  | Yen      | B09C 1/002 405/128.5 |
| 7,204,660 | B2 | * | 4/2007  | Shulgin  | B09C 1/08 405/128.75 |
| 2011/0139695 | A1 | * | 6/2011 | Borden   | B09C 1/002 210/170.07 |
| 2011/0153213 | A1 | * | 6/2011 | Buchanan | B09C 1/105 702/2     |

* cited by examiner

*Primary Examiner* — John Kreck
(74) *Attorney, Agent, or Firm* — Timothy Harney; Daniel Park; John T. Lucas

(57) ABSTRACT

A method of remediation at a remediation site having one or more undesirable conditions in which one or more soil characteristics, preferably soil pH and/or elemental concentrations, are measured at a remediation site. A trace element humate surfactant composition is prepared comprising a humate solution, element solution and at least one surfactant. The prepared trace element humate surfactant composition is then dispensed onto the remediation site whereby the trace element humate surfactant composition will reduce the amount of undesirable compounds by promoting growth of native species activity. By promoting native species activity, remediation occurs quickly and environmental impact is minimal.

22 Claims, 2 Drawing Sheets

REMEDIATION USING TRACE ELEMENT HUMATE SURFACTANT

GOVERNMENT RIGHTS

The U.S. Government has rights in this invention pursuant to Contract No. DE-AC07-05ID14517, between the U.S. Department of Energy (DOE) and the Battelle Energy Alliance.

FIELD OF THE INVENTION

The present invention relates to remediation of an identified site by dispensing a prepared trace element humate surfactant composition to promote the growth of native species reducing the amount of undesirable conditions at the identified site.

BACKGROUND

The remediation of a site having undesirable conditions such as hydrocarbon, heavy metal, and solvent contaminated wetland environments is an important topic. Pollution can affect soils and wetland areas through settled air emissions, accidental spills and direct discharges. Remediation of wetland areas is exceedingly difficult due to the fragile ecosystem, remote locations, and difficult terrain. Current techniques for removing oil from contaminated coastlines and oceans do not lend themselves to the wetland areas due to the abrupt and destructive nature of these techniques. There are three current primary methods for removing oil contamination from wetlands: 1) removing a significant portion of the top layer of soil, a difficult task in a marshy area and devastating to the ecosystem; 2) using high pressure water to blast the oil out of the wetlands in the hope of sending it to more open areas for capture, collection and disposal which ultimately can destroy the fragile ecosystem taking decades to recover; 3) allowing natural processes to reclaim the wetlands over a period generally lasting decades. As none of these remediate the area quickly without causing damage to the area, there is a need for a method of remediation that is both timely and environmentally safe for the ecosystem.

BRIEF SUMMARY

One or more embodiments relate to a method for remediation of a site having at least one undesirable condition. A preferred embodiment comprises the following steps: 1) measuring one or more organic characteristics of the remediation site, the remediation site having at least one undesirable condition, including but not limited to hydrocarbon, hydraulic fracking solutions, heavy metal, and solvent contamination; 2) preparing a trace element humate surfactant composition comprising a humate solution, an element solution, and at least one surfactant; and 3) dispensing the trace element humate surfactant onto the remediation site so that the trace element humate surfactant composition will promote the growth of at least one native species that will reduce the amount of undesirable conditions.

In a preferred embodiment, the step of measuring one or more organic characteristics includes measuring the pH of the remediation site. The step of preparing a trace element humate surfactant composition comprising a humate solution, an element solution, and at least one surfactant, includes that the humate solution comprises humic acid and humate salts. The pH of the prepared trace element humate surfactant composition is approximately the same as the measured pH of the remediation site, thereby promoting the growth of native species which will reduce the amount of undesirable conditions.

In another preferred embodiment, the step of measuring one or more organic characteristics includes measuring the concentration of one or more elements from the group of nitrogen, phosphorous, and iron. The step of preparing a trace element humate surfactant composition then includes preparing an element solution comprising one or more elements from the group of nitrogen, phosphorous, and iron so that the concentration of these added elements are approximately equal to the element concentrations measured at the remediation site, thereby promoting the growth of native species which will reduce the amount of undesirable conditions.

In yet another preferred embodiment, the step of measuring organic characteristics includes measuring both pH and element concentration of the remediation site. In this embodiment, the trace element humate surfactant composition comprises a humate solution and an element solution; where the humate solution comprises humic acid and humate salts so that the pH of the trace element humate surfactant composition is approximately equal to the measured pH of the remediation site; and where the element solution comprises nitrogen and phosphorous so that the element concentration of the trace element humate surfactant composition is approximately equal to the measured elements of the remediation site, thereby promoting the growth of native species which will reduce the amount of undesirable conditions.

In a preferred embodiment, the step of preparing a trace element humate surfactant composition preferably comprises a humate solution, an element solution, and at least one surfactant, where the one surfactant comprises at least one saponin.

The multiple embodiments described herein have many advantages, including but not limited to those described above. However, embodiments do not require that all advantages and aspects be incorporated into every embodiment of the present invention.

BRIEF DESCRIPTION OF THE DRAWINGS

These and other features, aspects, and advantages of the embodiments will become better understood with reference to the following description, appended claims, and accompanied drawings where:

DETAILED DESCRIPTION

Figure 1:
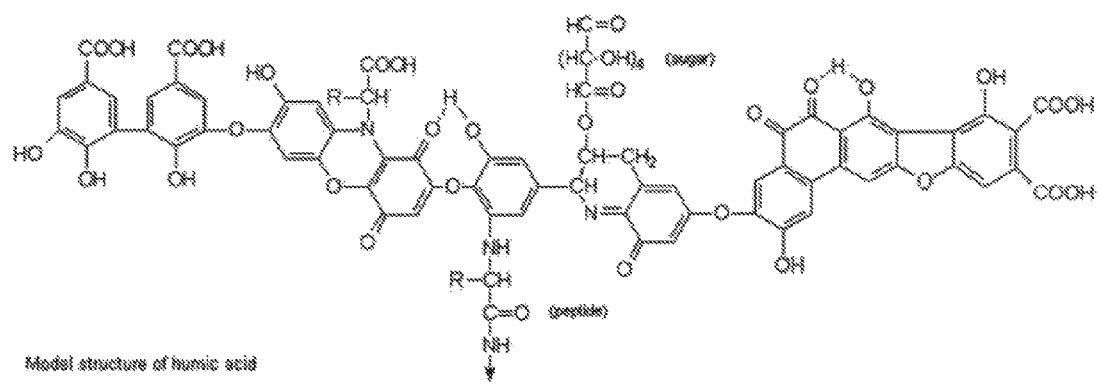
FIG. 1 is a schematic diagram of one embodiment of a model structure of humic acid.
Figure 2:
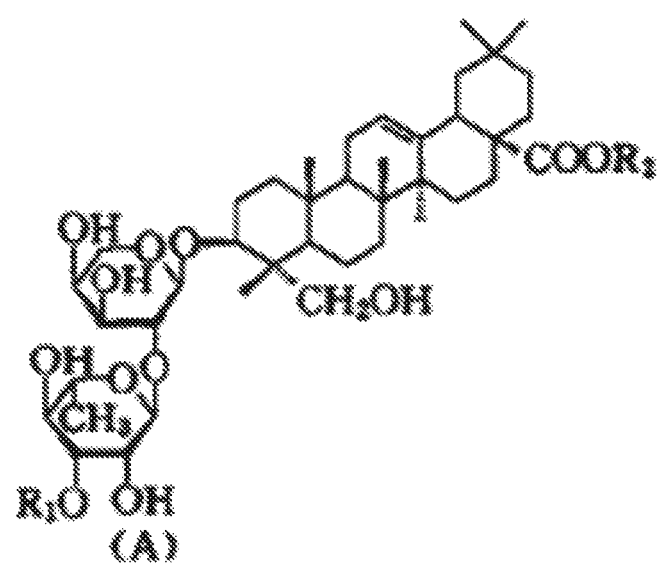
FIG. 2 is a schematic diagram of one embodiment of a model structure of saponin.

A method of remediation using a trace element humate surfactant composition where the remediation site contains one or more undesirable conditions.

A preferred embodiment includes remediation of undesirable conditions of an environmental site through a method comprising the following steps: 1) Measuring one or more organic characteristics of the remediation site, the remediation site having at least one undesirable condition, including but not limited to hydrocarbon, heavy metal, and solvent contamination. 2) Preparing a trace element humate surfactant composition comprising a humate solution, an element solution, and at least one surfactant. 3) Dispensing the trace element humate surfactant onto the remediation site so that the trace element humate surfactant composition will promote the growth of at least one native species that will reduce the amount of undesirable conditions.

One or more embodiments relate to a method for remediation using a trace element humate surfactant composition. A preferred embodiment comprises the above mentioned steps and further includes measuring the pH of the remediation site prior to the preparation of the trace element humate surfactant composition. In this preferred embodiment, the trace element humate surfactant composition is prepared so that the pH of the prepared trace element humate surfactant composition is approximately the same as the measured pH of the remediation site allowing for compatibility with the pH of the remediation site.

In another preferred embodiment, the step of measuring one or more organic characteristics includes measuring the concentration of one or more elements from the group of nitrogen, phosphorous, and iron. In this preferred embodiment, the step of preparing a trace element humate surfactant composition includes preparing an element solution comprising one or more elements from the group of nitrogen, phosphorous, and iron. If nitrogen is included in the element solution, the concentration of nitrogen is in the range of greater than 0 up to and including 20 percent by volume. If phosphorous is included in the element solution, the concentration of phosphorous is in the range of greater than 0 up to and including 20 percent by volume. If iron is present in the element solution, the concentration of iron is in the range between greater than 0 up to and including 5 percent by volume. The concentrations of these elements are included in the element solution so that the concentration of these added elements are approximately equal to the element concentrations measured at the remediation site.

In another preferred embodiment, the step of measuring organic characteristics includes measuring both pH and element concentrations at the remediation site. The humate solution comprises humic acid and humate salts so that the pH of the trace element humate surfactant composition is approximately equal to the measured pH of the remediation site. The element solution comprises nitrogen and phosphorous so that the element concentration of the trace element humate surfactant composition is approximately equal to that of the measured elements at the remediation site.

In yet another preferred embodiment, the step of preparing a trace element humate surfactant composition preferably comprises a humate solution, an element solution, and at least one surfactant, where the one surfactant comprises at least one saponin.

One or more embodiments are directed to a method for using a described composition for hydrocarbon remediation. In one preferred embodiment, the soil composition of the remediation site is measured. It is preferred in these embodiments that the organic characteristics measured comprise the pH and element concentration of the remediation site. A trace element humate surfactant composition is prepared containing a humate solution, an element solution and at least one surfactant. The humate solution comprising humic acid, fulvic acid, and humate salts. The element solution comprising at least one element from the group of elements including nitrogen, phosphorous, and iron. The prepared trace element humate surfactant composition is then dispensed onto the remediation site, promoting the growth of native microbial activity which reduces the amount of undesirable compounds.

In yet another embodiment, the soil pH of the remediation site is measured. The pH measurements are used to prepare a trace element humate surfactant composition which comprises a humate solution comprising a humic acid concentration range of 0 to 50 percent by volume of the humate solution, a humate salt concentration range of 0 to 30 percent by volume of the humate solution, and a pH that is approximately equal to the measured pH of the remediation site soil. In this embodiment, the humate solution has a concentration range of 0.5% to 10% by volume of the trace element humate surfactant composition. In another embodiment, the humate solution concentration range is preferably 1-2% by volume of the trace element humate surfactant composition. These concentration ranges provide optimal microbial growth and activity; once over 5% concentration by volume, the trace element humate surfactant composition will still promote microbial activity, however to a lesser degree.

One or more embodiments involve measuring the element concentrations of soil at a remediation site. These element concentrations are then used to determine the recipe for an element solution as the element concentrations of the element solution will be similar to the measured element concentrations of the remediation site. The element solution preferably has a concentration of nitrogen that is approximately equal to the measured concentration of nitrogen from soil at the remediation site. The nitrogen preferably has a concentration range of greater than zero to 20% by volume of the trace element humate surfactant composition. The element solution will also have a concentration of phosphorus that is approximately equal to the measured concentration of phosphorus from soil at the remediation site. The phosphorus preferably has a concentration range of greater than zero to 20% by volume of the trace element humate surfactant composition.

In other preferred embodiments, the element solution will also contain iron in a concentration range of greater than zero to 5% by volume of the trace element humate surfactant composition.

Other embodiments of the method for remediation include the measurement of the organic characteristics at the remediation site. Then the preparation of a trace element humate surfactant composition comprising a humate solution, an element solution, and a surfactant. In these embodiments, the surfactant of the trace element humate surfactant composition comprises at least one saponin. This saponin comprises a polycyclic aglycone, which comprises sapogenin and/or saraponin.

In one or more embodiments, the measurements of the organic characteristics are performed either before or after the contamination of the remediation site. Preferably, when using measurements performed before contamination, meaning on the environmental site before acquiring the undesirable conditions, these soil characteristics are stored and used for reference in the event of contamination.

Trace Element Humate Surfactant Composition

Trace element humate surfactant composition is a remediation composition comprising a humate solution, an element solution, and at least one surfactant. The unique components of the trace element humate surfactant composition allow for an increased activity of native microbes which leads to remediation of contaminants at a remediation site. Preferably, the composition of the trace element humate surfactant composition comprises (in percent by volume of the trace element humate surfactant) 0.5-10% humate solution, greater than 0 to 45% element solution, and the remaining percentage comprises surfactant.

Humate Solution

The humate solution is a mixture that comprises humic acid, fulvic acid, and humate salts. The humic acid comprises aromatic and heterocyclic structures, carboxyl groups, and phenolate groups while functioning as a dibasic or tribasic acid. The humic acid acts as a catalyst for enzymes in the soil of the remediation site that are used in the degradation process. Fulvic acid is preferably a natural constituent of the soil humus at the remediation site and the fulvic acid is formed from the decomposition of cellular material and preferably acts as a natural chelator of minerals and metals in soil at the remediation site. Both humic and fulvic acid, in the presence of nitrogen, phosphorous, and/or iron, preferably stimulate native species activity at the remediation site.

In some embodiments the humate solution has a concentration range of about 0.5-10 percent by volume of the trace element humate surfactant composition. In preferred embodiments, the humate solution comprises 1-2 percent concentration of the trace element humate surfactant composition. The humic acid has a concentration range of greater than 0 to 50 percent by volume of the humate solution. The humate salts have a concentration in the range of greater than 0 to 30 percent by volume of the humate solution.

Element Solution

The element solution is a mixture comprising at least one element selected from the group of nitrogen, phosphorous, potassium, calcium, magnesium, chlorine, sodium, sulfur, manganese, copper, molybdenum, zinc and iron. In preferred embodiments, the element solution is a mixture comprising at least one element selected from the group of phosphorous, nitrogen, and iron. In some embodiments, the element solution is prepared so that the concentration of elements in the element solution approximately equals the concentration of elements measured in the remediation site. In one or more embodiments, the nitrogen is present in a range between 0 to 20 percent by volume of the trace element humate surfactant composition. The nitrogen will aid in plant growth. In certain preferred embodiments, the element solution contains phosphorous in a range between 0 to 20 percent by volume of the trace element humate surfactant composition. The concentration range of phosphorous in the trace element humate surfactant composition is approximately equal to the measured concentration of phosphorous at the remediation site. Keeping a phosphorous concentration approximately equal to that measured at the remediation site will benefit plant health by its role in photosynthesis, nutrient transport, and energy transfer. In certain preferred embodiments, the element concentration of iron in the element solution is in the range of 0 to 5 percent by volume of the trace element humate surfactant composition. Preferably, iron is less than 5 percent by volume of the trace element humate surfactant composition as higher concentrations of iron have detrimental effects on environment.

Preferably, the trace element humate surfactant composition remediates an area by placing the area in the same condition as it was before the presence of the undesirable characteristics; an overabundance of plant growth due to excess element solution concentrations is an unwanted result; therefore, using element concentrations in the trace element humate surfactant composition that are approximately equal to the measured element concentrations of the remediation site is ideal. With nitrogen, any more than the 20 percent by volume and too much plant growth occurs after remediation, something that should be avoided when restoring the remediation site back to its original state. However, in some embodiments, it is desirable to use an amount of element in excess of that measured in the remediation site is used to help aid in overall plant health while remediation is ongoing.

Surfactant

A surfactant is a compound that lowers the surface tension between two liquids or between a liquid and a solid. The surfactant allows the humate solution to absorb the contaminants in the water and soil, enhancing the microbial activity. In some embodiments, the surfactant comprises at least one saponin, preferably a polycyclic aglycone that comprises at least a sapogenin and/or a saraponin. The surfactant comprises the remaining percent by volume of the trace element humate surfactant composition. In preferred embodiment, the surfactant comprises 45-65% by volume of the trace element humate surfactant composition. Preferably, the surfactant weighs less than the contaminants and water allowing the trace element humate surfactant composition to remain on the surface.

Remediation Site

For the purposes of the disclosed embodiments, a remediation site is any site that contains one or more undesirable conditions. The remediation site comprises soil, groundwater, sediment, surface water, and other land forms or water bodies. In preferred embodiments, the remediation site comprises a wetland, an area saturated with water either permanently or seasonally, consisting of hydric soil and supports aquatic plants. In a preferred embodiment, the remediation site comprises a wetland with hydrocarbons, preferably an oil spill.

Undesirable Conditions

The remediation site contains at least one undesirable condition, preferably at least one from the group of hydrocarbon, hydraulic fracking solutions, heavy metal, solvent, and salt contamination. The contamination of the remediation site is preferably assessed by a number of different ways including, but not limited to total petroleum hydrocarbon concentration of the remediation site whereas total petroleum hydrocarbon concentration is preferably measured to the parts per million for determining hydrocarbon contamination. In preferred embodiments, undesirable conditions are determined by gathering a plurality of samples from a plurality of sample sites, and comparing these sample results to ecotoxological screening benchmark concentrations for the remediation site. Threshold Effect Concentrations (TECs) and Probable Effect Concentrations (PECs) are preferably used to determine if conditions are undesirable and to what extent. TECs are concentrations below which adverse effects would not be expected while PECs are concentration above which adverse effects are probable.

Organic Characteristics

In one or more embodiments, the remediation site preferably comprises one or more organic characteristics from the group including, but not limited to pH, humic acid, humate salts, fulvic acid, exchangeable acidity, and element concentrations. In one or more embodiments, the organic characteristics are measured prior to the remediation of the contaminants.

In one or more embodiments, at least one remediation site organic characteristic is measured. To measure the acidity or alkalinity of the remediation site, pH is preferably measured through any number of standard procedures, more preferably saturated paste extract, diluting the sample of the remediation site with water or calcium chloride and then measuring on a standard laboratory pH meter. Measurements of other organic characteristics preferably include nutrient/element content, percentage of organic matter, and cation exchange capacity. In the measuring process, samples are preferably taken from multiple places within the remediation site as to best represent the entire remediation site. There are also several standard practices for the measurement of elements in soil including, but not limited to, soil extraction with 1 Molar HCl and then determined with an atomic absorption spectrophotometer.

Native Species

A native species is any living organism that is or was naturally occurring at the remediation site. Preferably, the native species is a microbe or biological agent such as a bacterium or fungus that occurs naturally at the remediation site. Preferably, the native species is Alcanivorax, Bacillus cereus or Methylocella Silvestris.

The preferred native species is preferably identified by sampling the native species of the remediation site and determining which native species is optimal for remediating the undesirable conditions. Preferably, factors such as growth rate, consumption rate, by-product produced by the native species, impact on the environment, and long term viability are used in selecting the preferred native species. A higher growth rate and consumption rate are preferred for rapid remediation, while a low environmental impact and non-toxic residue or mineralized materials as byproducts are preferred characteristics.

The step of identifying one or more native species in a determined remediation site comprises a number of known microbial identification methods including but not limited to DNA chipping, media selection, colony morphology, biochemical and enzymatic tests, serological methods, microscopic examination, and molecular methods. The identified microbes are compared to a catalogue of microbes to select those native species which naturally mitigate the undesirable conditions.

To determine if a native species has undergone growth, growth of the native species is preferably measured in size of species, quantity of species, and/or activity of species. In order to identify the organic characteristics that promote the growth of at least one of the native species in a remediation site, there are several methods known in the art which are used. These include but are not limited to growing the native species on a series of nutrient agar cultures in several different nutrient concentrations in order to identify the nutrients that promote growth. In another embodiment, the native species is preferably grown on agar with a combination of nutrients in several concentration ranges in order to determine the conditions that will promote growth. Another embodiment uses an enzymatic test that preferably starts with the isolation of the species and the use of a substrate, such as an enzymatic sugar, or amino acid, to see if the substrate promotes species growth. In a preferred embodiment, the substrate used would be selected from the components of the trace element humate surfactant composition.

Natural Mitigation of Damage

The natural mitigation of the undesirable conditions at the remediation site comprises the breakdown of the undesirable conditions by an identified native species. In a preferred embodiment, a native species of microbes naturally digests hydrocarbon ring structures, using the hydrocarbon molecules for fuel.

Dispensing of Trace Element Humate Surfactant Composition

Preferably, the prepared trace element humate surfactant composition is dispensed from above onto the remediation site until the trace element humate surfactant composition forms an approximately uniform layer on top of the remediation site. The approximately uniform layer on the remediation site is a layer of trace element humate surfactant composition that is preferably judged by the human eye to be as equally distributed as possible across the remediation site; more preferably, the approximately uniform layer has a thickness variation of distributed trace element humate surfactant composition that is less than 25% across the remediation site. Even more preferably, the thickness variation of distributed trace element humate surfactant composition is less than 10% across the remediation site. There are several embodiments for dispensing the trace element humate surfactant composition, including but not limited to: spray, aerial drop, pumping through an apparatus that resembles a fire hose, placing upstream and allowing the current to bring the trace element humate surfactant composition to the remediation site or a combination thereof. A preferred embodiment uses a fire hose like apparatus to spray the trace element humate surfactant composition onto the remediation site. Distributing the trace element humate surfactant composition by way of these preferred embodiments carries an advantage as there is not a need to enter the remediation site, limiting further damage to the sensitive environmental area being remediated.

Having described the basic concept of the embodiments, it will be apparent to those skilled in the art that the foregoing detailed disclosure is intended to be presented by way of example. Accordingly, these terms should be interpreted as indicating that insubstantial or inconsequential modifications or alterations and various improvements of the subject matter described and claimed are considered to be within the scope of the spirited embodiments as recited in the appended claims. Additionally, the recited order of the elements or sequences, or the use of numbers, letters or other designations therefor, is not intended to limit the claimed processes to any order except as may be specified. All ranges disclosed herein also encompass any and all possible subranges and combinations of subranges thereof. Any listed range is easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as up to, at least, greater than, less than, and the like refer to ranges which are subsequently broken down into sub-ranges as discussed above. As utilized herein, the terms "about," "substantially," and other similar terms are intended to have a broad meaning in conjunction with the common and accepted usage by those having ordinary skill in the art to which the subject matter of this disclosure pertains. As utilized herein, the term "approximately equal to" shall carry the meaning of being within 15, 10, 5, 4, 3, 2, or 1 percent of the subject measurement, item, unit, or concentration, with preference given to the percent variance. It should be understood by those of skill in the art who review this disclosure that these terms are intended to allow a description of certain features described and claimed without restricting the scope of these features to the exact numerical ranges provided. Accordingly, the embodiments are limited only by the following claims and equivalents thereto. All publications and patent documents cited in this application are incorporated by reference in their entirety for all purposes to the same extent as if each individual publication or patent document were so individually denoted.

We claim:
1. A method for remediation comprising:
   a. measuring one or more organic characteristics of a remediation site, said organic characteristics consisting of at least one characteristic from the group of: humic acid concentration, humate salts concentration, fulvic acid concentration, and element concentrations, whereby said remediation site comprises one or more undesirable conditions;
   b. preparing a trace element humate surfactant composition comprising at least one organic characteristic approximately equal in percent concentration to at least one said measured organic characteristic; said trace element humate surfactant composition comprising:
      i. a humate solution comprising humic acid, fulvic acid, and humate salts;
      ii. an element solution comprising at least one element from the group of elements consisting of: nitrogen, phosphorous, potassium, calcium, magnesium, chlorine, sodium, sulfur, manganese, copper, molybdenum, zinc and iron; and
      iii. at least one surfactant; and
   c. dispensing said prepared trace element humate surfactant composition onto said remediation site, whereby said trace element humate surfactant composition will reduce the amount of said undesirable conditions at said remediation site which may cause damage by promoting the growth of at least one native species at said remediation site.

2. The method of claim 1 wherein said undesirable conditions includes hydrocarbon saturation.

3. The method of claim 1 further comprising identifying a remediation site comprising one or more undesirable conditions.

4. The method of claim 3 further comprising:
   a. identifying said at least one native species at said identified remediation site which naturally mitigate damage caused by said undesirable conditions; and
   b. identifying said organic characteristics that promote growth of at least one said identified native species at said identified remediation site which naturally mitigate damage caused by said undesirable conditions at said identified remediation site; and whereby:
   c. said measuring said one or more organic characteristics comprises measuring one or more organic characteristics of said identified remediation site, whereby said identified remediation site comprises one or more said undesirable conditions.

5. The method of claim 1, wherein said prepared trace element humate surfactant composition is dispensed onto said remediation site until said remediation site is exposed to a layer of said prepared trace element humate surfactant composition.

6. The method of claim 1 wherein said element concentrations include at least one element from the group of nitrogen, phosphorous, and iron.

7. The method of claim 3 wherein said undesirable conditions comprise at least one condition from the group of hydrocarbon, hydraulic fracking solutions, heavy metal, solvent, and salt contamination.

8. The method of claim 4 wherein said identifying one or more native species at said identified remediation site which naturally mitigate damage caused by said undesirable conditions further comprises:
   a. sampling said native species at said identified remediation site;
   b. determining at least one optimal native species for remediation of undesirable conditions, wherein said optimal native species comprises at least one factor from the group of native species growth rate, native species rate of consumption, long term viability of said native species, by-product produced by said native species, and said native species' impact on the environment.

9. The method of claim 1, wherein:
   said step of preparing trace element humate surfactant composition wherein said humate solution comprises
      i. said humic acid with a concentration range between and including 0 to 50 percent by volume of said humate solution; and
      ii. said humate salts with a concentration range between and including 0 to 30 percent by volume of said humate solution.

10. The method of claim 9 wherein said concentration of said humate solution is between and including 0.5 to 10 percent by volume of said trace element humate surfactant composition.

11. The method of claim 9 wherein said concentration of said humate solution is between and including 1 to 2 percent by volume of said trace element humate surfactant composition.

12. The method of claim 9 wherein said humate salts comprise sodium and potassium.

13. The method of claim 1, wherein:
   a. said step of measuring one or more said organic characteristics comprises measuring element concentrations of said remediation site;
   b. said step of preparing a trace element humate surfactant composition comprising said element solution comprising one or more elements from the group of nitrogen, phosphorus, and iron wherein:
      i. said nitrogen is present in a range between 0 to 20 percent, including 20 percent, by volume of said trace element humate surfactant composition so that the concentration of said nitrogen is approximately equal to said measured concentration of nitrogen of said remediation site; and
      ii. said phosphorus is present in a range between 0 to 20 percent, including 20 percent, by volume of said trace element humate surfactant composition so that the concentration of said phosphorus is approximately equal to said measured concentration of phosphorus of said remediation site.

14. The method of claim 13 wherein said step of preparing an element solution further comprises adding iron, wherein said iron is present in a range of zero to five percent by volume of said trace element humate surfactant composition so that the concentration of said iron is approximately equal to said measured concentration of iron of said remediation site.

15. The method of claim 1, wherein said surfactant of said trace element humate surfactant composition comprises at least one saponin, wherein: a. said saponin comprises a polycyclic aglycone; and b. said polycyclic aglycone comprises at least one member of the following group: sapogenin and saraponin.

16. The method of claim 15, wherein said trace element humate surfactant composition is able to float on the contaminants and water as to remain in contact with the surface of the remediation site.

17. The method of claim 9, wherein:
said step of preparing trace element humate surf composition further wherein said trace element humate surfactant composition comprises said humate solution and an element solution wherein:
  i. said humate solution comprises humic acid and humate salts wherein:
    1. said humic acid with a concentration range between and including 0 to 50 percent by volume of said humate solution; and
    2. said humate salts with a concentration range between and including 0 to 30 percent by volume of said humate solution;
  ii. said element solution comprises nitrogen and phosphorous wherein:
    1. said nitrogen is present in a range between 0 to 20 percent, including 20 percent, by volume of said trace element humate surfactant composition so that the concentration of said nitrogen is approximately equal to said measured concentration of nitrogen of said remediation site; and
    2. said phosphorus is present in a range between 0 to 20 percent, including 20 percent, by volume of said trace element humate surfactant composition so that the concentration of said phosphorus is approximately equal to said measured concentration of phosphorus of said remediation site.

18. The method of claim 17, wherein said surfactant of said trace element humate surfactant composition comprises at least one saponin wherein:
  a. said saponin comprises a polycyclic aglycone; and
  b. said polycyclic aglycone comprises at least one member of the following group: sapogenin and saraponin.

19. The method of claim 17 wherein said concentration of said humate solution is between and including 0.5 to 10 percent by volume of said trace element humate surfactant composition.

20. The method of claim 17 wherein concentration of said humate solution is between and including 1 to 2 percent by volume of said trace element humate surfactant composition.

21. The method of claim 18, wherein said trace element humate surfactant composition is able to float on the contaminants and water as to remain in contact with the surface of the remediation site.

22. A method for remediation comprising:
  a. measuring at least pH of a remediation site, whereby said remediation site comprises one or more undesirable conditions;
  b. preparing a trace element humate surfactant composition comprising at least a pH approximately equal to at least said pH of said remediation site; said trace element humate surfactant composition comprising:
    i. a humate solution comprising humic acid, fulvic acid, and humate salts;
    ii. an element solution comprising at least one element from the group of elements consisting of: nitrogen, phosphorous, potassium, calcium; magnesium, chlorine, sodium, sulfur, manganese, copper, molybdenum, zinc and iron; and
    iii. at least one surfactant; and
  c. dispensing said prepared trace element humate surfactant composition onto said remediation site, whereby said trace element humate surfactant composition will reduce the amount of said undesirable conditions at said remediation site by promoting the growth of at least one native species at said remediation site.

* * * * *